(12) United States Patent
Chandler

(10) Patent No.: US 8,194,956 B2
(45) Date of Patent: Jun. 5, 2012

(54) MEDICAL IMAGING SYSTEM AND RELATED METHODS

(75) Inventor: Carol Chandler, Lakeland, FL (US)

(73) Assignee: Mylife Global, Inc., Lakeland, FL (US)

( * ) Notice: Subject to any disclaimer, the term of this patent is extended or adjusted under 35 U.S.C. 154(b) by 0 days.

(21) Appl. No.: 13/077,043

(22) Filed: Mar. 31, 2011

(65) Prior Publication Data

US 2011/0243406 A1   Oct. 6, 2011

Related U.S. Application Data

(60) Provisional application No. 61/319,459, filed on Mar. 31, 2010.

(51) Int. Cl.
*G06K 9/00* (2006.01)
(52) U.S. Cl. ........................ 382/128; 382/284
(58) Field of Classification Search .............. 382/128, 382/132, 173, 180, 282, 283, 284, 287, 318, 382/319
See application file for complete search history.

(56) References Cited

U.S. PATENT DOCUMENTS

| | | | | |
|---|---|---|---|---|
| 5,898,797 A * | 4/1999 | Weiss et al. | .................. | 382/199 |
| 6,487,271 B1 * | 11/2002 | Laurent | ...................... | 378/98.9 |
| 6,529,617 B1 * | 3/2003 | Prokoski | ...................... | 382/128 |
| 6,996,256 B2 * | 2/2006 | Pavlidis | ........................ | 382/118 |
| 2006/0110036 A1 * | 5/2006 | Luo et al. | ...................... | 382/170 |
| 2006/0184006 A1 | 8/2006 | Chen et al. | | |
| 2006/0262966 A1 | 11/2006 | Eck et al. | | |
| 2007/0110293 A1 | 5/2007 | Arnon | | |
| 2009/0318911 A1 | 12/2009 | Kaushal et al. | | |
| 2011/0243409 A1 * | 10/2011 | Naimi et al. | ................. | 382/128 |

OTHER PUBLICATIONS

International Searching Authority, PCT Transmittal of International Search Report and The Written Opinion mailed Nov. 23, 2011; entire report.

* cited by examiner

*Primary Examiner* — Andrew W Johns
(74) *Attorney, Agent, or Firm* — Allen, Dyer, Doppelt, Milbrath & Gilchrist, P.A.

(57) ABSTRACT

A medical imaging system includes an imaging device, an input device, an output device, and an imaging system server in signal communication with the imaging device, the input device and the output device, the imaging system server including at least one processor and machine readable memory. The server is configured to display a capture outline, the capture outline including a depiction of a body area to be imaged, display a preliminary image together with the capture outline such that the preliminary image is superimposable with the capture outline, and capture an image associated with the capture outline.

20 Claims, 7 Drawing Sheets

(6 of 7 Drawing Sheet(s) Filed in Color)

MEDICAL IMAGING SYSTEM AND RELATED METHODS

CROSS-REFERENCE TO RELATED APPLICATION

This application claims the benefit of U.S. Provisional Application Ser. No. 61/319,459, filed on Mar. 31, 2010.

FIELD OF THE INVENTION

The invention relates to medical imaging systems and methods, and more particularly, to systems and methods for thermal imaging for medial and other diagnostic purposes.

BACKGROUND OF THE INVENTION

The use of thermal imaging, or thermography, as a diagnostic tool is well known. However, it can be difficult for doctors and other diagnosticians to accurately and reliably associate a given thermal image of a patient with an underlying cause. Part of this difficulty can stem from uncertainty in the spatial relationship between thermal features of the image and bodily systems of the patient. Similar difficulties can arise in connection with the employment of other medical imaging systems, as well.

SUMMARY OF THE INVENTION

In view of the foregoing, it is an object of the present invention to provide improved medical imaging systems and methods. According to an embodiment of the present invention, a medical imaging system includes an imaging device, an input device, an output device, and an imaging system server in signal communication with the imaging device, the input device and the output device, the imaging system server including at least one processor and machine readable memory. The server is configured to display a capture outline, the capture outline including a depiction of a body area to be imaged, display a preliminary image together with the capture outline such that the preliminary image is superimposable with the capture outline, and capture an image associated with the capture outline.

According to aspects of the present invention, the imaging device is a thermal imaging device and the preliminary image is a real-time thermal image communicated to the imaging system server by the imaging device.

According to another aspect of the present invention, the imaging system server is further configured to superimpose an anatomical overlay over the captured image. The anatomical overlay is advantageously mapped to the capture outline. According to a further aspect of the present invention, the capture outline is a generally transparent mask of the area to be captured.

According to a method aspect, a computer-based medical imaging method includes displaying a capture outline corresponding to an body area to be imaged, displaying a preliminary image together with the capture outline such that the preliminary image is superimposable with the capture outline, and capturing an image associated with the capture outline.

These and other objects, aspects and advantages of the present invention will be better appreciated in view of the drawings and detailed descriptions of preferred embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF A PREFERRED EMBODIMENT

Figure 1:
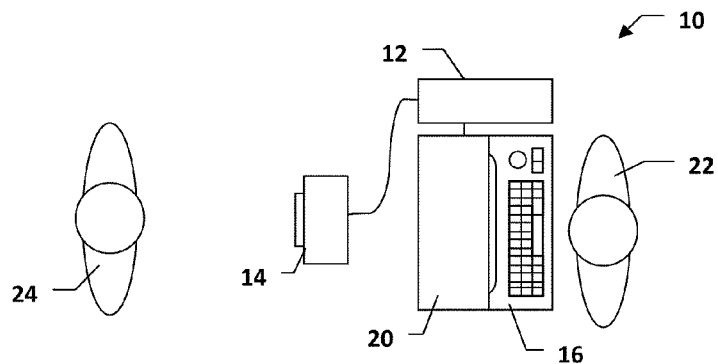
FIG. 1 is a schematic overview of a medical imaging system, according to an embodiment of the present invention.

Referring to FIG. 1, according to an embodiment of the present invention, a medical imaging system 10 includes an imaging system server 12, an imaging device 14, an input device 16 and an output device 20. The server 12 is in signal communication with the imaging device 14, input device 16 and output device 20. The system 10 is operable to allow a user 22 to capture an image of one or more areas of the body of a patient 24.

The server 12 includes at least one processor and machine readable memory and is configured to display a capture outline including a depiction of the body area to be imaged on the display 20, and to display a preliminary image of the patient 24 on the display 20 such that the preliminary image and the capture outline can be superimposed to ensure proper positioning of the patient 24 in the captured image. The server 12 is further configured to capture an image of the body area using the imaging device.

The present invention is not necessarily limited to any particular number, type or configuration of processors, nor to any particular programming language, memory storage format or memory storage medium. In implementations of the server 12 involving multiple processors and/or storage media, the system is not necessarily limited to any particular geographical location or networking or connection of the processors and/or storage media. Additionally, it is not necessarily required that the processors and/or storage be commonly owned or controlled. Likewise, the system 10 is not necessarily limited to any particular geographical location or networking or connection imaging, input and output devices 14, 16, 20.

The imaging device 14 can include any type of medical imaging device, such as a thermal imaging camera that is operable to capture images of the infrared signature of body areas of the patient. The camera and/or the server 12 can be configured to visually represent the imaged thermal signature using a plurality of colors corresponding to detected temperatures. Where a thermal imaging camera 14 is used as the medical imaging device, the preliminary image is preferably a real-time thermal image from the camera 14, such that as the patient 24 moves the user can see the real-time thermal image move relative to the capture outline.

Where the imaging device 14 is of a type where it is not practical and/or safe to use a preliminary image generated thereby, a secondary imaging device could be included with the imaging device 14. For example, if the imaging device 14 were an X-ray machine, then a video camera could be included oriented such that the body area covered by the video image correlated to the body area that would be X-rayed.

The input device 16 can include, for example, a keyboard, a mouse or other pointing device, a touch screen display, a voice input module or other device allowing inputs from a user 22 to be supplied to a computer system. The input device 16 can include a plurality of input devices, and can also include devices that accept inputs from computer systems remote from the server 12 and other system components—for instance, via communication over a network such as the Internet.

The output device 20 preferably includes some type of visual display, such as a computer monitor, and can also include a printer and a plurality of other output devices. The output device 20, like the input device 16, can include devices that accept inputs from computer systems remote from the server 12 and other system components, such that captured images can be output thereto for review and analysis.

Figure 2:
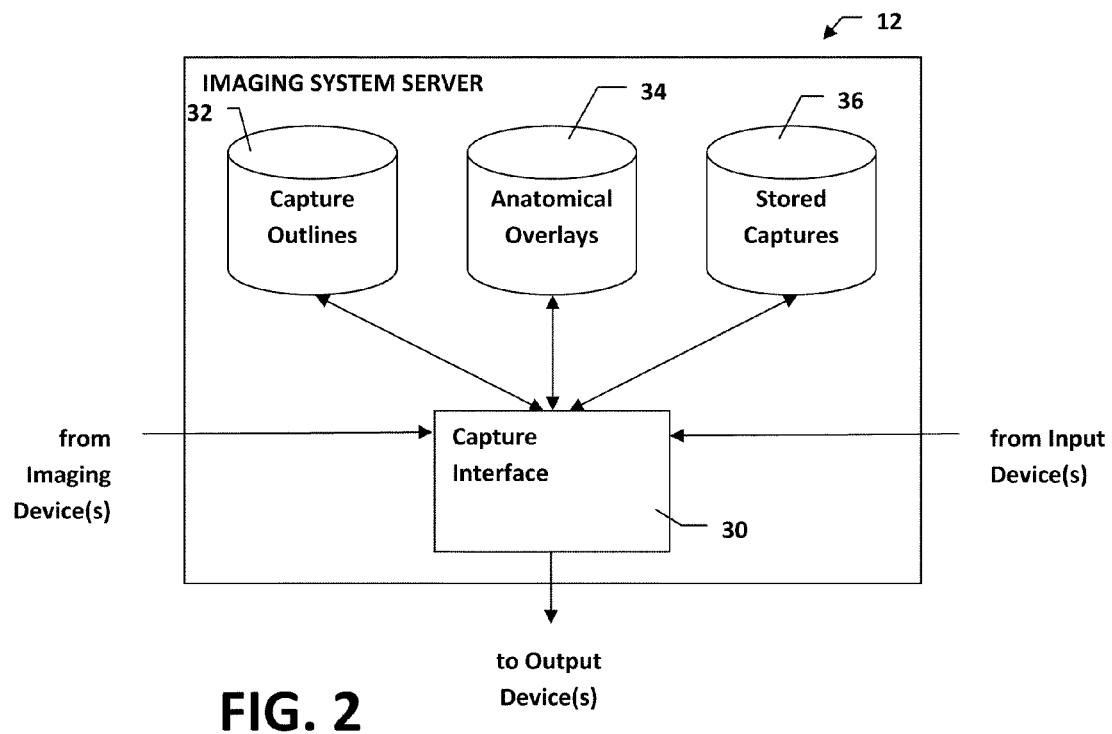
FIG. 2 is a schematic overview of an imaging system server of the medical imaging system of FIG. 1.

Referring to FIG. 2, the server 12 is preferably configured to execute a capture interface module 30 and databases of capture outlines 32, anatomical overlays 34 and stored captures 36. The capture interface 30 receives inputs from the input device 16 to display a selected capture outline from the database 32 via the output device 20. The capture interface 30 also receives the preliminary image from the imaging device 14 and displays it together with the selected capture outline so that the user 22 can use the capture outline as a guide to position the patient 24 prior to image capture.

When the user 22 is satisfied with the positioning of the preliminary image, the capture interface 30 can receive an instruction to capture an image via the imaging device 14. The capture interface 30 can allow the selection, via the input device 16, of one or more anatomical overlays from the database 34 to superimpose on the captured image. The stored captures are stored in the database 36 and can also be exported through a network connected export device to other computer systems. The stored captures can include only the captured image, or the captured image together with one or more overlays.

Referring to FIG. 3-6, an exemplary interface screen 40 generated by the capture interface 30 includes a capture viewing section 42, a capture control section 44 and a capture outline selection section 46. The capture viewing section 42 is used to display capture outlines, preliminary images, captures images and/or anatomical overlays. The capture control section 44 includes controls allowing the user 22 to control operation of the imaging device, including adjusting the focus and capturing a particular image capture, as well as post capture functions like saving the capture and exporting the capture.

Figure 3:
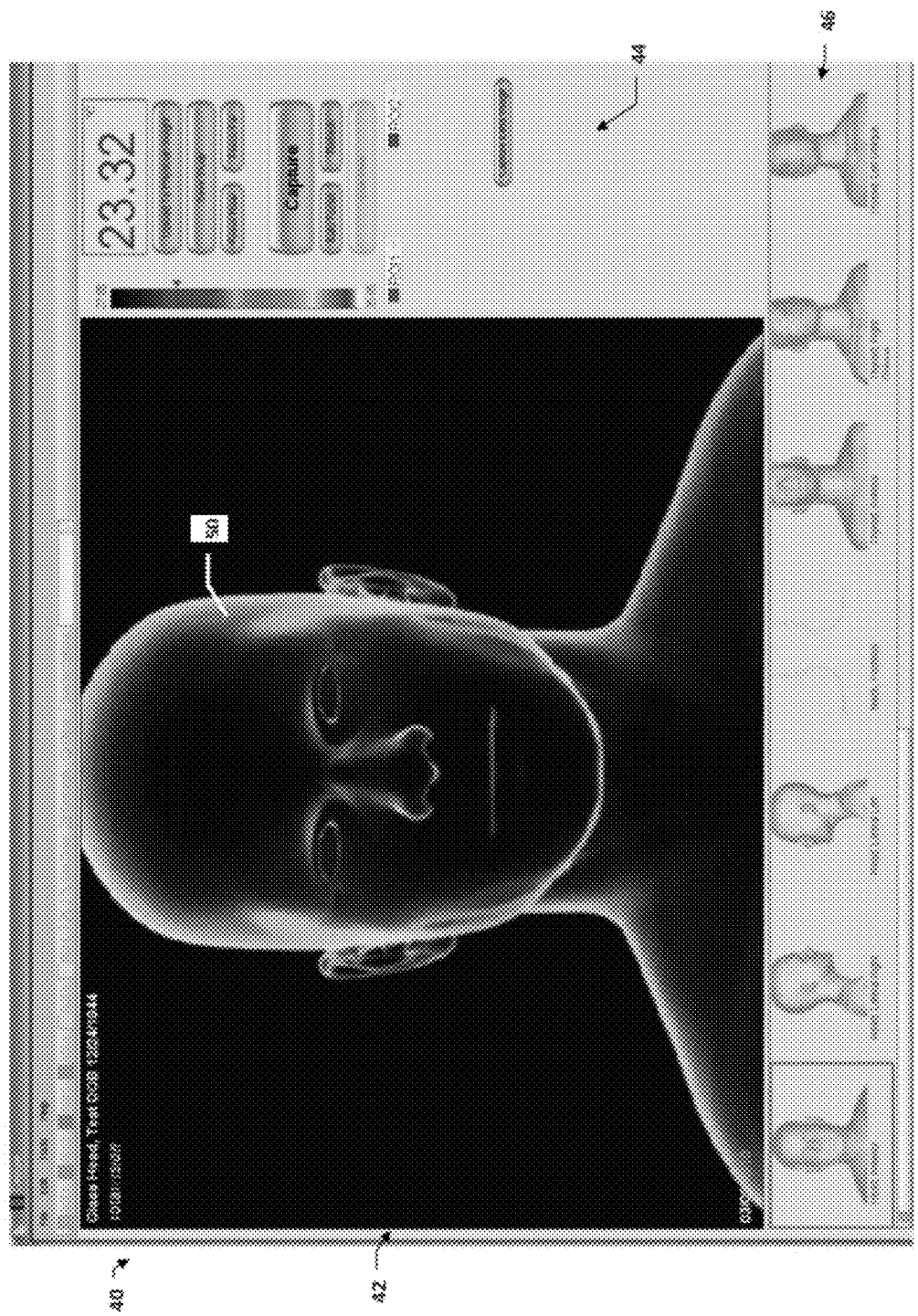
FIGS. 3-6 are screen views generated by the imaging system of FIG. 1.

In FIG. 3, the capture outline is a generally transparent mask 50 of a body area to be images. As used herein, "mask" refers generically to a three-dimensional representation of the exterior of the body area to be imaged, and is not specifically limited to representations of the face or any other specific body area. For instance, masks of legs, arms or torso could be displayed, or a mask of the entire body. The three-dimensional representation allows a technician operating the system 10 a very precise guide of what body area is to be captured and the proper orientation thereof.

The depicted mask 50 is a generic mask not necessarily corresponding to a specific patient. Alternately, the system 10 could utilize patient-specific masks. For instance, a doctor could take digital pictures of specific areas and orientations for which subsequent imaging was desired, the pictures could be uploaded to the system 10 and masks could be generated from the pictures. For instance, the transparency of the picture could be set sufficiently low to allow superimposition with the preliminary image.

Additionally, for a given capture category, corresponding, for instance, to a general body area, a plurality of masks for a plurality of predetermined orientations can be predetermined. An example of this is illustrated in the outline selection section 46, where a plurality of masks for various orientations for head and neck imaging are displayed. Accordingly, a doctor could simply specify capture category, such as "head and neck," and the technician would select that category and capture images associated with each capture outline provided for that category. As can be seen in FIG. 3, the mask 50 in the capture viewing section 42 was selected from the outline selection section 46.

In addition to the head and neck, other advantageous capture categories can include torso and extremities. Further category divisions could be made—for instance, torso could be divided into breast, chest, abdomen and back, and extremities into upper and lower extremities. The capture interface preferably displays a list of capture categories and then displays a plurality of the capture outlines based on the category selection.

Figure 4:
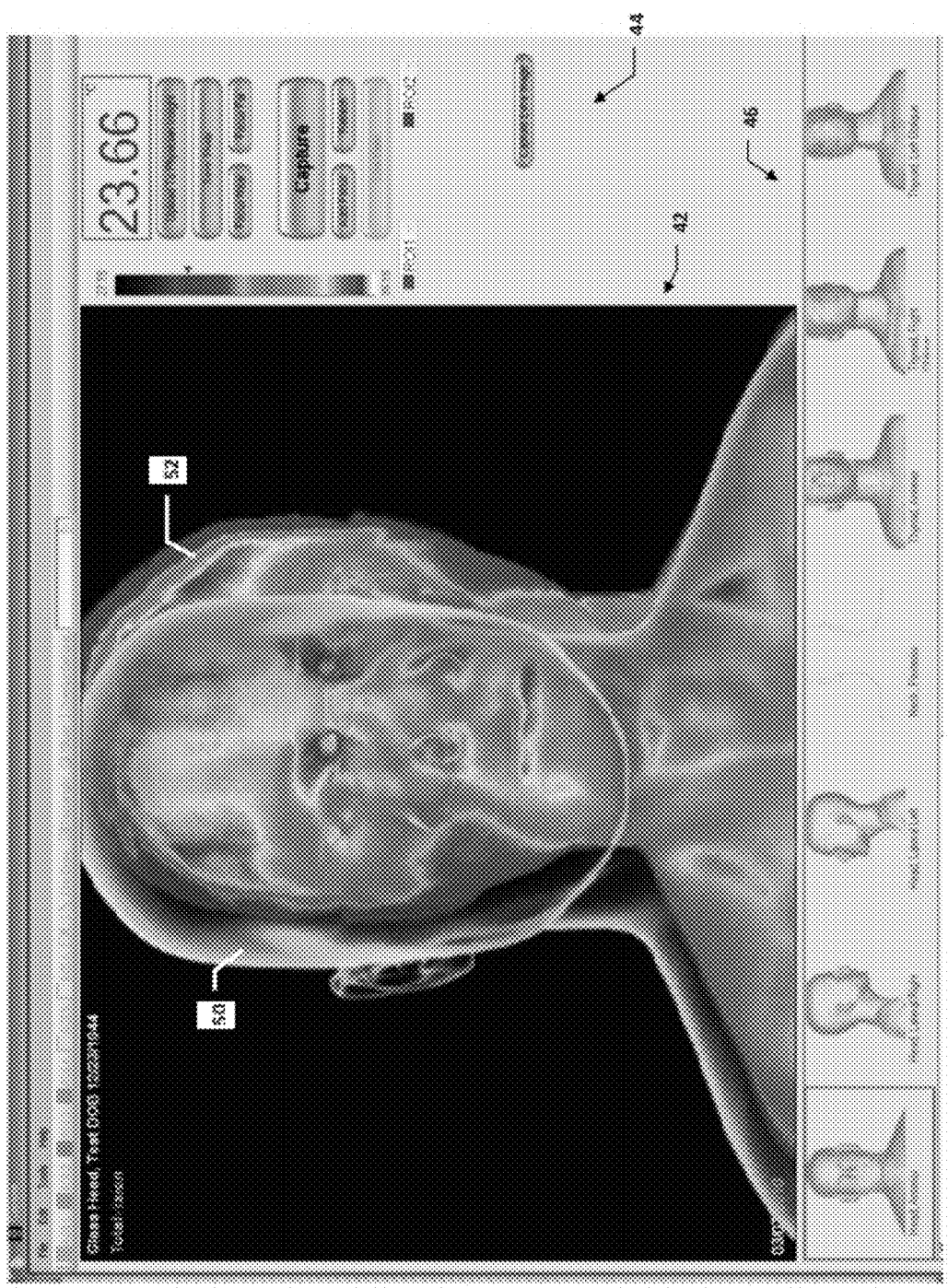
Figure 5:
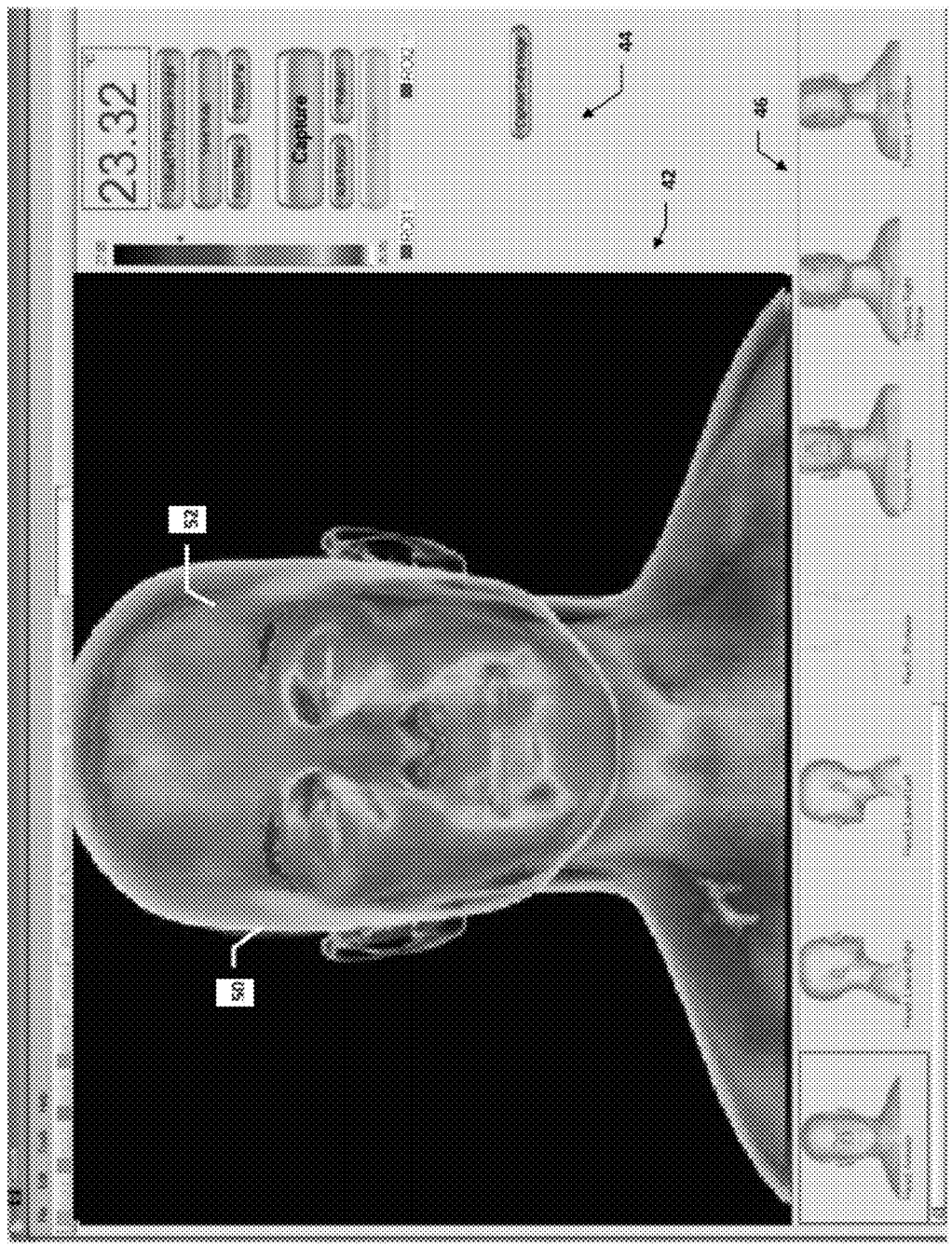

Referring to FIG. 4, the preliminary image 52 is now superimposed with the mask 50 in the capture viewing section 42. As will be appreciated therefrom, the preliminary image 52 is not aligned with the mask 50, and the user is able to adjust the position of the patient before capturing an image. In FIG. 5, the proper alignment has been achieved between the mask 50 and the preliminary image 52.

Figure 6:
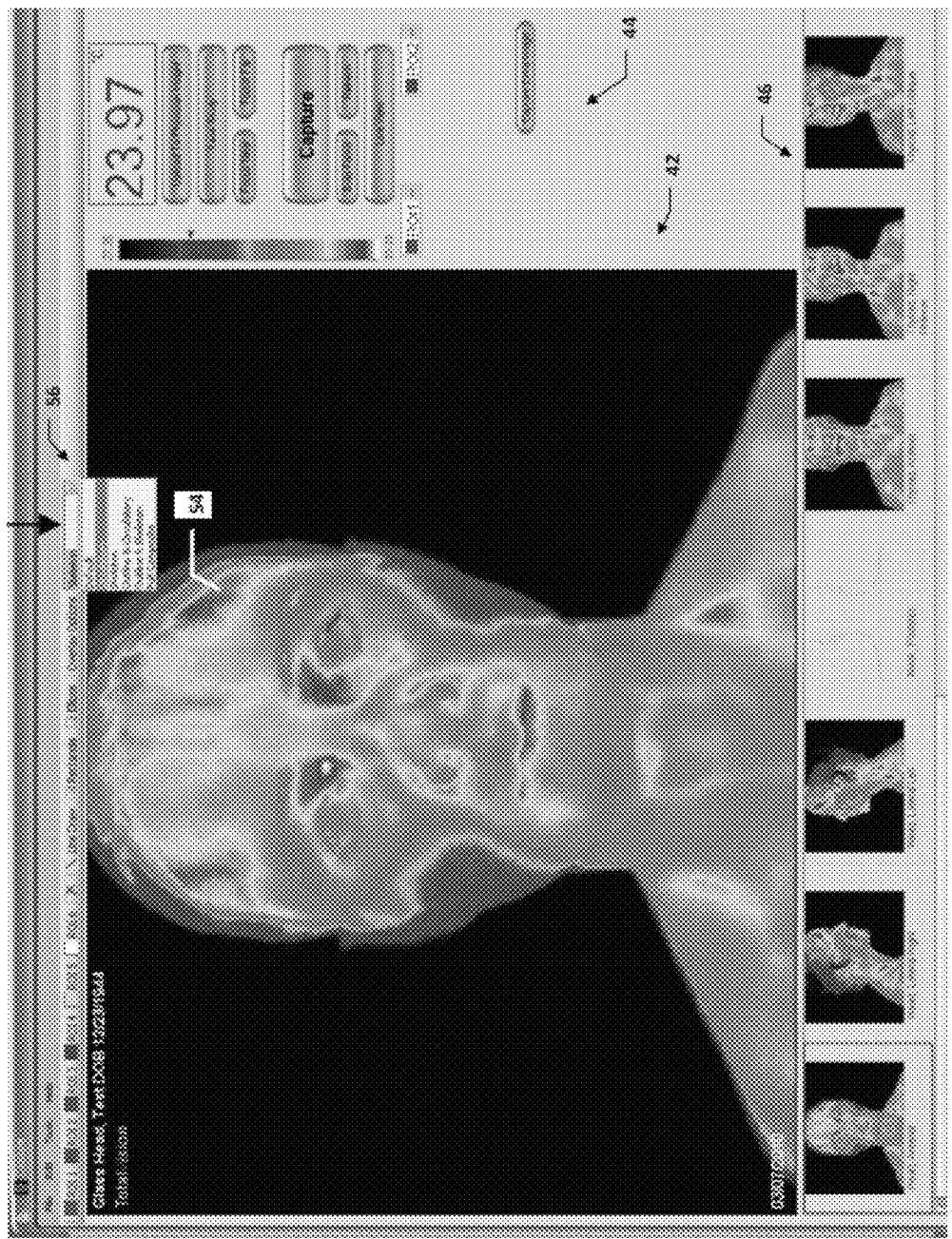

Referring to FIG. 6, the captured image 54 is shown in the capture viewing section 42. The mask 50 can be hidden to allow unobstructed viewing of the captured image 54. However, the mask 50 can also remain superimposed over the captured image 54 to assist in correlation of image features with external physical features. Additionally, a "thumbnail," or smaller version, of the captured image replaces the outline in the outline selection section 46, allowing the user to readily track which captures have already been taken. Advantageously, all of the saved captures for a given category and/or for a given patient can be saved and associated together as a group.

The interface screen 40 additionally includes an anatomical overlay selection 56 that displays a plurality of anatomical overlays for selection by the user. The selection 56 can also be used to show or hide the mask 50. Multiple body systems can be overlain on the captured image.

Figure 7:
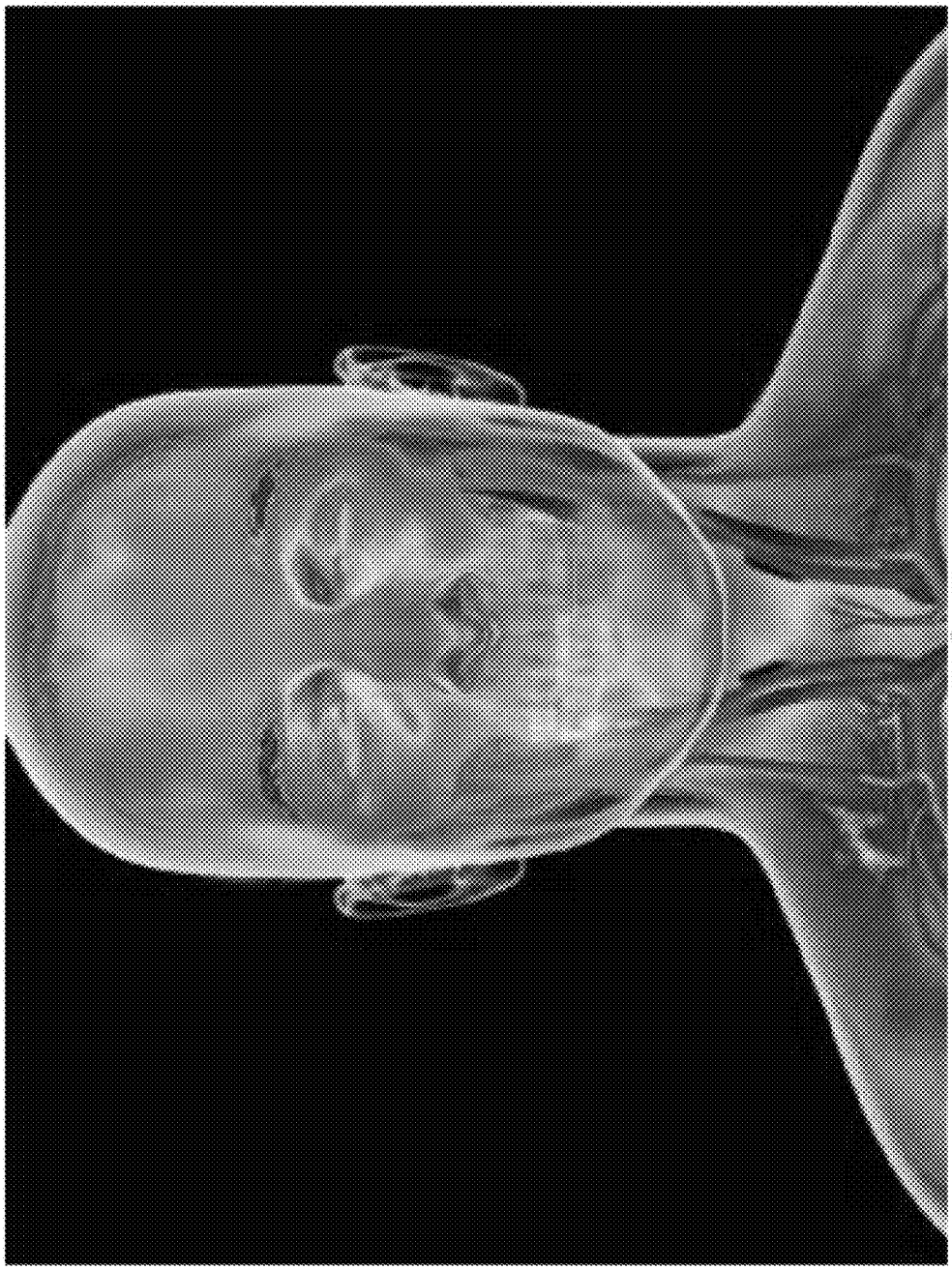
FIGS. 7 and 8 are thermal images with anatomical overlays associated therewith, generated by the imaging system of FIG. 1.
Figure 8:
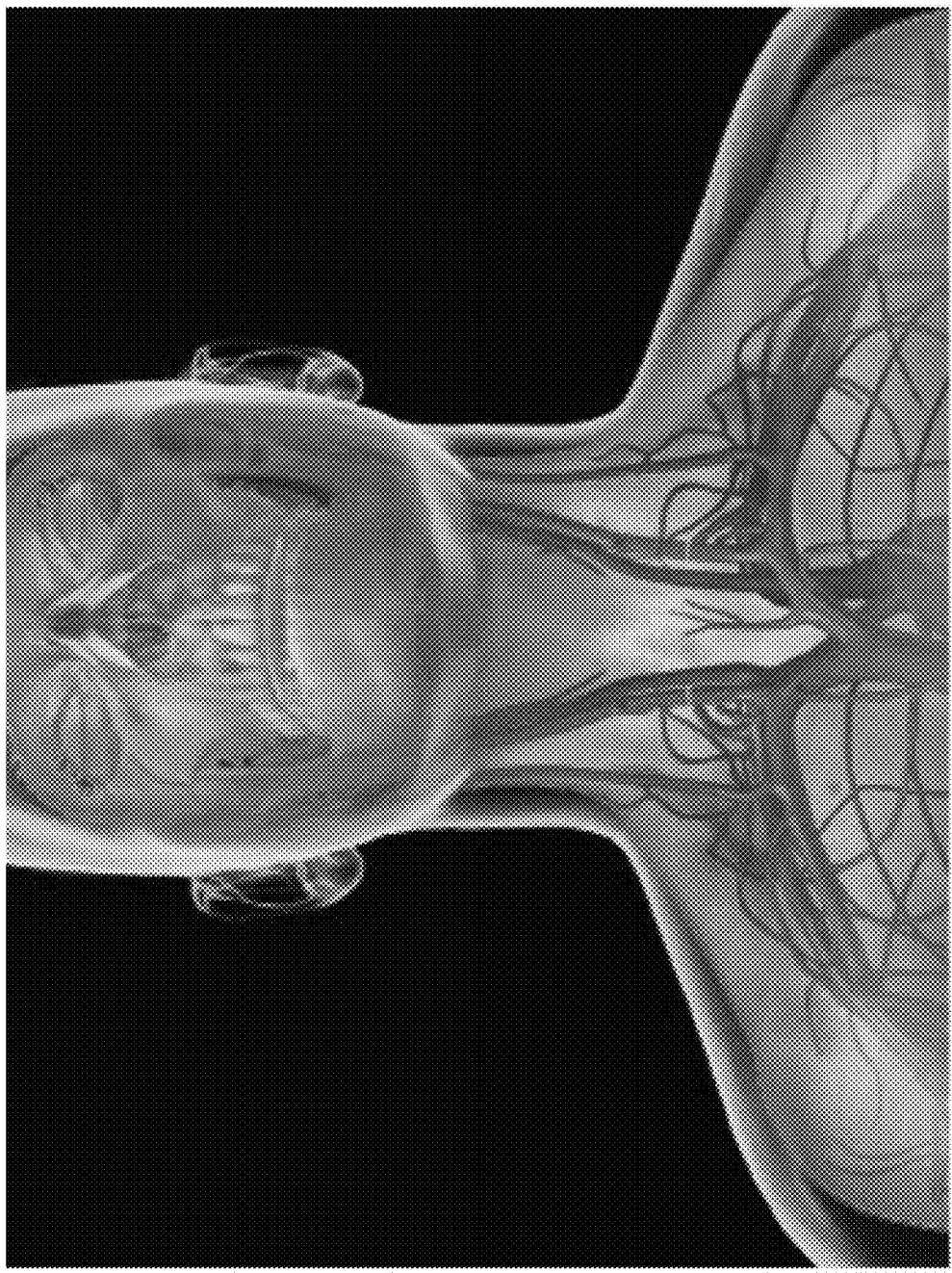

Referring to FIGS. 7 and 8, captured images with superimposed anatomical overlays can be seen, as well as superimposed masks. Advantageously, each anatomical overlay is mapped to a respective capture outlines/masks. Because the captured image is taken after alignment of a preliminary image with the capture outline, the location of the anatomical overlay on a given captured image can be accurately reflected by locating the overlay relative to the associated outline (whether or not the outline is actually shown).

In FIGS. 7 and 8, the anatomical overlays are generic overlays not necessarily corresponding to a specific patient. Alternately, the anatomical overlays can be patient specific. For example, a group of captured thermal images of a patient could be overlaid with previously captured X-ray images taken using the same capture guides.

Where generic overlays are used, the overlays selectable for a given captured image can be varied depending on the previously selected capture category. For example, if head and neck capture guides were used, then selections of skeletal, circulatory, lymphatic, respiratory and endocrine systems could be displayed for selection by the user. Further overlay selection divisions could include respiratory-sinus and endocrine-thyroid. As another example, if torso capture guides were used, then selections of circulatory, respiratory, digestive, excretory, muscular, skeletal and lymphatic systems could be displayed. Further overly selection divisions could include circulatory-heart and excretory-urinary. If extremity capture guides were used, then selections of muscular, skeletal and nervous systems could be used.

It will be appreciated from the foregoing that medical imaging systems and methods according to the present invention can advantageously minimize or eliminate error in patient positioning for medical imaging, ensuring that captured images are as close as possible to those desired by doctors or other medical professionals. Additionally, the predictable positioning of patients in captured images allows the accurate association of anatomical overlays therewith.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described.

What is claimed is:

1. A medical imaging system comprising:
   an imaging device;
   an input device;
   an output device; and
   an imaging system server in signal communication with the imaging device, the input device and the output device, the imaging system server including at least one processor and machine readable memory and configured to:
   display a capture outline, the capture outline including a depiction of a body area to be imaged;
   display a preliminary image together with the capture outline such that the preliminary image is superimposable with the capture outline; and
   capture an image associated with the capture outline.

2. The system of claim 1, wherein the imaging device is a thermal imaging device.

3. The system of claim 2, wherein the preliminary image is a real-time thermal image communicated to the imaging system server by the imaging device.

4. The system of claim 1, wherein the capture outline is a generally transparent mask of the body area to be imaged.

5. The system of claim 1, wherein the imaging system server is further configured to superimpose an anatomical overlay over the captured image.

6. The system of claim 5, wherein the anatomical overlay is mapped to the capture outline associated with the captured image.

7. The system of claim 5, wherein the imaging system server is further configured to:
   display a selection of a plurality of anatomical overlays; and
   receive a selection of the anatomical overlay to be superimposed.

8. The system of claim 7, wherein the imaging system server is further configured to:
   display a plurality of capture categories;
   receive a selection of at least one of the plurality of capture categories;
   display a plurality of capture outlines corresponding to the selected capture category; and
   receive a selection of the capture outline to be displayed;
   wherein the displayed selection of the plurality of anatomical overlays is determined based on the at least one selected capture category.

9. A computer-based medical imaging method comprising:
   displaying a capture outline corresponding to an a body area to be imaged;
   displaying a preliminary image together with the capture outline such that the preliminary image is superimposable with the capture outline; and
   capturing an image associated with the capture outline.

10. The method of claim 9, wherein capturing the image associated with the capture outline includes capturing a thermal image.

11. The method of claim 10, wherein displaying the preliminary image includes displaying a real-time thermal image.

12. The method of claim 9, wherein displaying the capture outline includes displaying a mask of the area to be captured.

13. The method of claim 9, further comprising superimposing an anatomical overlay over the captured image.

14. The method of claim 13, wherein superimposing the anatomical overlay over the captured image includes locating the anatomical overlay relative to the capture outline associated with the captured image.

15. The method of claim 13, further comprising:
   displaying a selection of a plurality of anatomical overlays;
   receiving a selection of the anatomical overlay to be displayed from among the plurality of anatomical overlays.

16. The method of claim 15, further comprising:
   displaying a plurality of capture categories;
   receiving a selection of at least one of the plurality of capture categories;
   displaying a plurality of capture outlines based upon the at least one selected capture category; and
   receiving a selection of the capture outline to be displayed from the plurality of capture outlines;
   wherein displaying the selection of the plurality of anatomical overlays includes determining the selection to be displayed based upon the at least one selected capture category.

17. A thermal imaging system comprising:
   a thermal imaging camera;
   an input device;
   a display; and
   an imaging system server in signal communication with the camera, the input device and the display, the imaging system server including at least one processor and machine readable memory and configured to:
   display a capture outline, the capture outline including a generally transparent mask of a body area to be imaged;
   display a real-time thermal image from the camera such that the real-time image is superimposable with the capture outline;
   capture a thermal image associated with the capture outline; and
   superimpose an anatomical overlay over the captured image, the anatomical overlay being mapped to the capture outline associated with the thermal image.

18. The system of claim 17, wherein the imaging system server is further configured to:
   display a selection of a plurality of anatomical overlays; and
   receive a selection of the anatomical overlay to be superimposed.

19. The system of claim 18, wherein the imaging system server is further configured to:
   display a plurality of capture categories;
   receive a selection of at least one of the plurality of capture categories;
   display a plurality of capture outlines corresponding to the selected capture category; and
   receive a selection of the capture outline to be displayed;

wherein the displayed selection of the plurality of anatomical overlays is determined based on the at least one selected capture category.

20. The system of claim 18, wherein the plurality of anatomical overlays includes at least one of: a skeletal system overlay, a circulatory system overlay, a nervous system overlay, a muscular system overlay, a lymphatic system overlay, a respiratory system overlay, a digestive system overlay, a lymphatic system overlay, an endocrine system overlay, and an excretory system overlay.

\* \* \* \* \*